United States Patent
Moszner et al.

(10) Patent No.: US 7,816,476 B2
(45) Date of Patent: Oct. 19, 2010

(54) POLYMERIZABLE CYCLOPROPYL ACRYLATES

(75) Inventors: Norbert Moszner, Eschen (LI); Frank Zeuner, Vaduz (LI); Urs-Karl Fischer, Arbon (CH); Volker M. Rheinberger, Vaduz (LI); Armin de Meijere, Göttingen (DE); Viktor Bahutski, Göttingen (DE)

(73) Assignee: Ivoclar Vivadent AG, Schaan (LI)

( * ) Notice: Subject to any disclaimer, the term of this patent is extended or adjusted under 35 U.S.C. 154(b) by 154 days.

(21) Appl. No.: 11/200,488

(22) Filed: Aug. 9, 2005

(65) Prior Publication Data

US 2006/0178469 A1 Aug. 10, 2006

(30) Foreign Application Priority Data

Feb. 7, 2005 (DE) .................. 10 2005 005 541

(51) Int. Cl.
- *C08F 20/06* (2006.01)
- *C07D 335/04* (2006.01)
- *C07D 409/02* (2006.01)
- *C07D 311/00* (2006.01)
- *C07D 307/87* (2006.01)
- *C07C 69/74* (2006.01)
- *A61K 6/00* (2006.01)

(52) U.S. Cl. .................. 526/317.1; 549/23; 549/49; 549/396; 549/462; 560/119; 523/120

(58) Field of Classification Search .................. 549/23, 549/49, 396, 462; 560/119; 523/120; 526/317.1
See application file for complete search history.

(56) References Cited

U.S. PATENT DOCUMENTS

2004/0077882 A1* 4/2004 Moszner et al. .............. 549/23

OTHER PUBLICATIONS

Meijere et al., "Synthesis and Radical Polymerization of Various 2 Cyclopropylacrylates," Eur. J. Org. Chem. 17:3669-3678 (2004).*

Meijere et al., "Synthesis and Radical Polymerization of Various 2-Cyclopropylacrylates," Eur. I Org. Chem. 17:3669-3678 (2004).

Moszner et al., "Polymerization of Cyclic Monomers, 12$^a$. Radical Polymerization of Substituted Methyl 2-(Bicyclo[3.1.0]hex-1-yl)Acrylates and Properties of Thereof Based Light-Curing Composites," Macromol. Mater. Eng. 291:83-89 (2006).

Oppolzer et al., "48. Palladium-Catalysed Intramolecular Cyclisations of Olefinic Propargylic Carbonates and Application to the Diastereoselective Synthesis of Enantiomerically Pure (—)-χ-Thujone," Helvetica Chimica Acta 80:623-639 (1997).

* cited by examiner

*Primary Examiner*—William K Cheung

(57) ABSTRACT

Cyclopropyl acrylate of general formula (1), constitutional and stereoisomers thereof and their mixtures Formula (1)

in which A is selected from:

$A^1$:

$A^2$:

26 Claims, No Drawings

POLYMERIZABLE CYCLOPROPYL ACRYLATES

The present invention relates to polymerizable cyclopropyl acrylates which are in particular suitable for preparing dental materials.

Radically polymerizable cyclic monomers are of particular interest because they exhibit significantly less polymerization shrinkage in comparison with linear monomers (R. K. Sadhir, R. M. Luck, Expanding Monomers, CRC Press, Boca Raton etc. 1992).

Unlike other known ring-opening monomers, such as methylene group-containing spiroorthocarbonates (SOCs), spiroorthoesters (SOEs) or bicyclic orthoesters (BOEs), vinyl cyclopropanes are not sensitive to moisture and their radical polymerization is also characterized in that polymers with a relatively high molar mass are obtained (N. Moszner, F. Zeuner, T. Völkel, V. Rheinberger, Macromol. Chem. Phys. 200 (1999) 2173). In the case of the radical polymerization of SOCs or SOES, polymers with carbonate-ether or ether-ether groups in the main chain are formed, which accordingly are easy to split hydrolytically or enzymatically. On the other hand the ring-opening polymerization of 1,1-disubstituted 2-vinyl cyclopropanes leads to polymers which contain only hydrolytically stable C—C bonds in the main chain.

EP 0 798 286 B1 discloses monomers with several vinyl cyclopropyl groups which lead to insoluble polymer networks.

Sanda et al. were able to show, taking the radical copolymerization of 1,1-bis(ethoxycarbonyl)-2-vinyl cyclopropane with methyl methacrylate (MMA) as an example, that in comparison with methacrylates vinyl cyclopropanes are characterized by a smaller radical polymerization capacity, which clearly restricts their practical use (F. Sanda, T. Takata, T. Endo, Macromolecules, 27 (1994) 3982).

Improved reactivity in the radical polymerization is shown by bicyclic cyclopropyl acrylates, such as e.g. 2-[bi-cyclo [3.1.0]hex-1-yl]-acrylic acid methyl esters (N. Moszner, F. Zeuner, U. K. Fischer, V. Rheinberger, A. de Meijere, V. Bagutski, Macromol. Rapid. Commun. 24 (2003) 269), the use of which in dental materials was proposed in DE 102 49 342 A1. However, the proposed structures are difficult to access and functionalizable only via the acrylic acid ester group.

The object of the invention is to provide monomers which exhibit a radical polymerization reactivity comparable with methacrylates and shrink little during polymerization.

This object is achieved by the cyclopropyl acrylates of general formula (1)

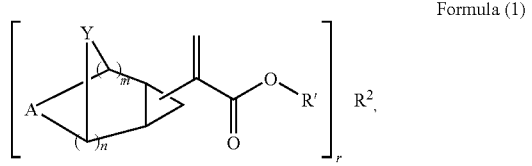

Formula (1)

in which A is selected from:

$A^1$:

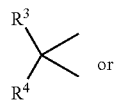

or $A^2$:

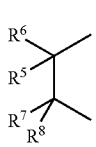

and the remaining variables have the following meanings independently of each other:

Y=for A=$A^1$: is absent, $CH_2$ or O, for A=$A^2$: $CH_2$ or O,
n=for Y is absent: 0, 1, 2 or 3, for Y=$CH_2$ or O: 1,
m=for Y is absent: 0, 1, 2 or 3, for Y=$CH_2$ or O: 1,
r=1, 2, 3 or 4,
$R^1$=H, a $C_1$ to $C_{10}$ alkyl, $C_6$ to $C_{12}$ aryl, $C_1$ to $C_{10}$ arylalkyl or bicyclic $C_5$-$C_{12}$ radical or —$R^{10}$—X—,
R=an aliphatic $C_1$ to $C_{20}$ hydrocarbon radical substituted r times by the expression in brackets which can be interrupted by O or S, cycloaliphatic $C_4$-$C_{12}$ radical, bicyclic $C_5$-$C_{12}$ radical, $C_6$-$C_{14}$ aryl or $C_7$-$C_{20}$ alkylaryl radical,
$R^3$=—CO—$OR^9$, —CO—$R^9$, —S(O)$R^9$, $SO_2R^9$, —$SO_2$($OR^9$), —PO($OR^9$)$_2$, —CN, —H, —$R^9$,
$R^4$=—CO—$OR^9$, —CO—$R^9$, —S(O)$R^9$, —$SO_2R^9$, —$SO_2$($OR^9$), —PO($OR^9$)$_2$, —CN or —$R^{11}$—$R^{10}$—X—,
$R^5$-$R^8$=independently of one another H, —CO—$OR^9$, —CO—$NHR^9$, —CO—$NR^9{}_2$, —CO—$R^9$, —CN, a $C_1$-$C_{20}$ alkyl radical, which can be interrupted by O or S, a cycloaliphatic $C_4$-$C_{12}$ radical, a bicyclic $C_5$-$C_{12}$ radical, a $C_6$-$C_{14}$ aryl $C_7$-$C_{20}$ alkylaryl radical, or at least two of the radicals form together with the carbon atoms to which they are bonded, a 5- to 8-membered ring system,
$R^9$=a $C_1$-$C_{20}$ alkyl radical which can be interrupted by O or S, a cycloaliphatic $C_4$-$C_{12}$ radical, a bicyclic $C_5$-$C_{12}$ radical, a $C_6$-$C_{14}$ aryl or $C_7$-$C_{20}$ alkylaryl radical,
$R^{10}$=is absent or a $C_1$-$C_{20}$ alkylene radical which can be interrupted by O or S, a cycloaliphatic or bicyclic $C_5$-$C_{12}$ radical, a $C_6$-$C_{14}$ arylene or $C_7$-$C_{20}$ alkylenearylene radical,
$R^{11}$=—COO—, —CO—, —SO—, —$SO_2$—, —$SO_2$(O—), —PO($OR^9$)(O—),
X=is absent, —O—CO—, —CO—O—, —NH—CO—, —CO—NH—, —NH—CO—O— or —O—CO—NH—, wherein X has the meaning "is absent" if $R^{10}$ is absent, and
wherein the radicals $R^2$ and $R^{5-9}$ can be substituted or unsubstituted, either $R^4$=—$R^{11}$—$R^{10}$—X— or $R^1$=—$R^{10}$—X— and the expression in brackets is bonded to $R^2$ via X.

If the cyclopropyl acrylate of general formula (1) contains several radicals of one type, for example several $R^9$ radicals, these can be identical or different.

As substituents of the radicals $R^2$ and $R^{5-9}$, alkyl, halogen, $OCH_3$, $OC_2H_5$, vinyl, (meth)acryl, $COOR^{12}$, $SiCl_3$, $Si(OR^{13})_3$, and/or mesogenic groups are preferred, wherein
$R^{12}$=H or $C_1$ to $C_{10}$ alkyl, $C_6$ to $C_{12}$ aryl, $C_6$ to $C_{10}$ arylalkyl or a bicyclic $C_5$-$C_{12}$ radical and
$R^{13}$=H or $C_1$ to $C_{10}$ alkyl radical.

Particularly preferred substituents are $C_1$-$C_3$ alkyl, $OCH_3$, (meth)acryl or $Si(OR^{13})_3$ with $R^{13}$=methyl or ethyl.

Formula (1) covers all the constitutional and stereoisomeric forms and mixtures of different constitutional and stereoisomeric forms, such as e.g. racemates. As can be seen from formula (1), the radical —C(═$CH_2$)—C(═O)—O—$R^9$ can be bonded to the cyclopropane ring via the bridge atom or preferably a bridgehead atom. The formula covers only compounds which are consistent with the chemical valency theory.

By arylalkyl groups is meant alkyl radicals which are substituted by one or more aryl groups and, accordingly, by alkylaryl groups is meant aryl groups which are substituted by one or more alkyl radicals. An alkylenearylene radical is a group which is composed of at least one alkylene group and at least one arylene group and is unsaturated at both the alkylene part and the arylene part, such as for example —$CH_2$-Ph-.

The feature that a radical can be interrupted by foreign atoms, such as oxygen or sulphur, is to be understood to mean that one or more of the foreign atoms are integrated into a carbon chain. It follows from this that the foreign atoms cannot be terminal, i.e. binding to neighbouring groups always takes place via a carbon atom, and that the number of foreign atoms must necessarily be smaller than the number of carbon atoms.

If Y is absent, the binding sites of the ring atoms are saturated by hydrogen.

Preferred cyclopropyl acrylates of formula (1) are compounds in which A=$A^1$, $R^1$=—$R^{10}$—X— and Y is absent (formula 2), compounds in which A=$A^1$, $R^4$=—$R^{11}$—$R^{10}$—X— and Y is absent (formula 3) and compounds in which A=$A^2$, $R^1$=—$R^{10}$—X— and Y is $CH_2$ or O (formula 4).

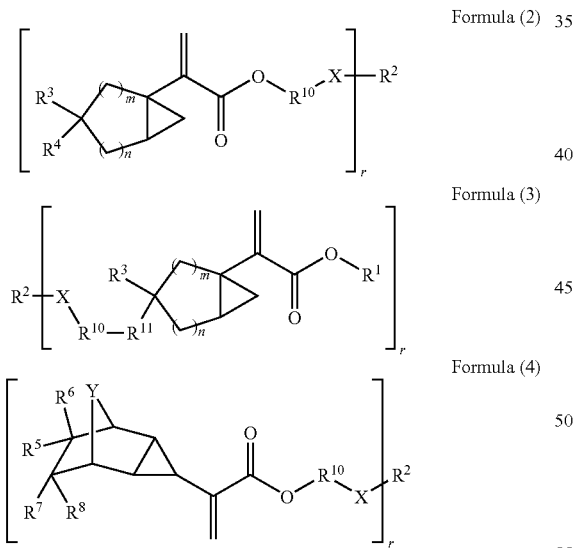

Formula (2)

Formula (3)

Formula (4)

The remaining variables have the meanings mentioned above in the case of formula (1). Compounds of formulae (2) and (3) are particularly preferred, compounds of formulae (2) being quite particularly preferred.

For the variables of formulae (1), (2), (3) and (4) the following definitions exist which can be chosen independently of one another:

Y=for A=$A^1$: is absent, for A=$A^2$: $CH_2$ or O,
n=1,
m=1,
r=1 or 2, $R^1$=H, $C_1$ to $C_5$ alkyl or bicyclic $C_5$-$C_{12}$ radical or in particular —$R^{10}$—X—, $R^2$=an aliphatic $C_1$-$C_6$ hydrocarbon radical which can be interrupted by O, a cycloaliphatic $C_6$-$C_8$ radical, a bicyclic $C_6$-$C_8$ radical, a $C_6$-$C_{10}$ aryl or $C_7$-$C_{10}$ alkylaryl radical, $R^3$=—CO—$OR^9$, —CO—$R^9$, $SO_2R^9$, CN, H or —$R^9$, $R^4$=—CO—$OR^9$, —CO—$R^9$, $SO_2R^9$, CN or —$R^{11}$—$R^{10}$—X—, $R^5$-$R^8$=independently of one another H, —CO—$OR^9$, —CO—$R^9$, CN, a $C_1$-$C_6$ alkyl radical which can be interrupted by O, a cycloaliphatic $C_6$-$C_8$ radical, a bicyclic $C_6$-$C_8$ radical, a $C_6$-$C_{10}$ aryl or $C_7$-$C_{10}$ alkylaryl radical, $R^9$=a $C_1$-$C_6$ alkyl radical which can be interrupted by O, a cycloaliphatic $C_6$-$C_8$ radical, a bicyclic $C_6$-$C_8$ radical, a $C_6$-$C_{10}$ aryl or $C_7$-$C_{10}$ alkylaryl radical, in particular $C_1$-$C_3$ alkyl, $R^{10}$=is absent or a $C_1$-$C_{10}$ alkylene radical which can be interrupted by O, a bicyclic $C_6$-$C_9$ radical, or $C_7$-$C_{10}$ alkylenearylene radical, in particular is absent or $C_1$-$C_6$ alkylene, $R^{11}$=—CO—O—, —CO— or —$SO_2$—, in particular —CO—O—.

X=is absent, —O—CO— or —CO—O—.

Cyclopropyl acrylates in which all the variables have one of the preferred meanings are particularly preferred.

The cyclopropyl acrylates according to the invention of general formula (2) ($R^{10}$, X is absent, m=1, n=1, r=1) can be obtained starting from O-alkyl-O'-(4-chloro-but-2-inyl)carbonates:

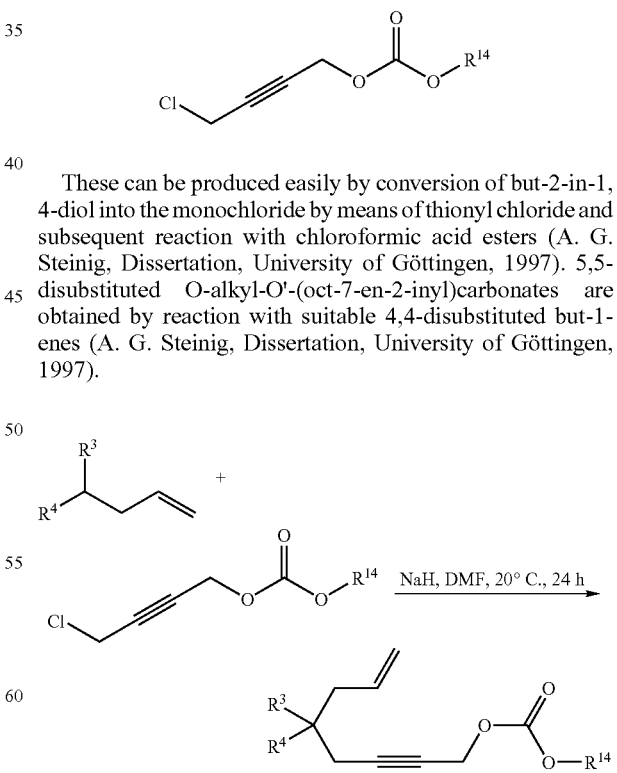

These can be produced easily by conversion of but-2-in-1,4-diol into the monochloride by means of thionyl chloride and subsequent reaction with chloroformic acid esters (A. G. Steinig, Dissertation, University of Göttingen, 1997). 5,5-disubstituted O-alkyl-O'-(oct-7-en-2-inyl)carbonates are obtained by reaction with suitable 4,4-disubstituted but-1-enes (A. G. Steinig, Dissertation, University of Göttingen, 1997).

Alternatively, the cyclopropyl acrylates according to the invention of general formula (2) ($R^{10}$, X is absent, m=1, n=1, r=1) can be produced in three stages starting from commercial 4-chloro-2-butin-1-ol. This produces corresponding 5,5-disubstituted O-alkyl-O'-(oct-7-en-2-inyl)carbonates by reaction with suitable 4,4-disubstituted but-1-enes and subsequent esterification with chloroformic acid methyl ester.

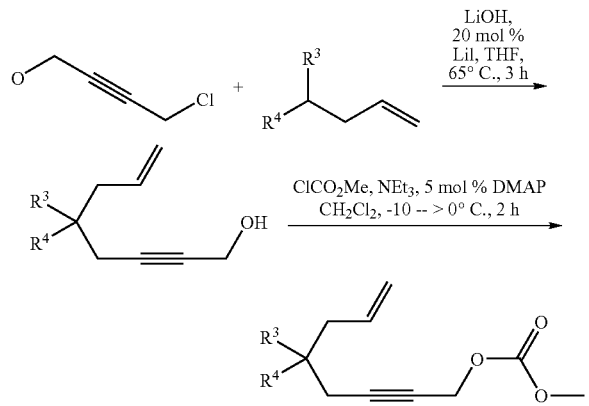

The next stage is a palladium-catalyzed four-stage cascade reaction, in which initially the five-membered, then the three-membered ring is formed, and finally the formed vinyl palladium complex is reacted with carbon monoxide and then an alcohol to produce the 3,3-disubstituted 2-(bicyclo[3.1.0]hex-1-yl)-acrylic acid ester of general formula (2) (R. Grigg, R. Rasul, J. Redpath, D. Wilson, Tetrahedron Lett. 37 (1996) 4609; W. Oppolzer, A. Pimm, B. Stammen, E. Hume, Helv. Chim. Acta, 80 (1997) 623:

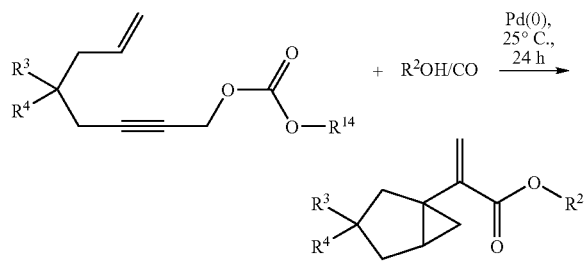

Specific Example:

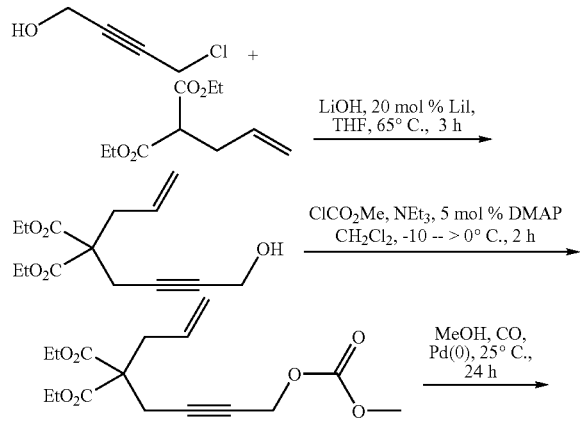

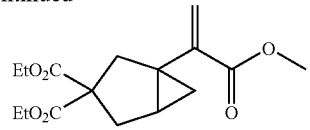

Cyclopropyl acrylates of general formula (2) (r>1) can be obtained by hydrolysis of cyclopropylacrylic acid methyl esters (r=1 and $R^{10}$, X=is absent) and subsequent esterification with polyfunctional alcohols [(HO—$R^{10}$—X—)$_r$]:

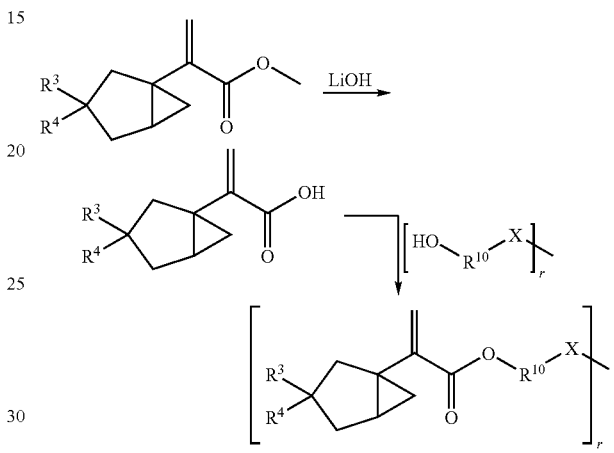

Specific Example:

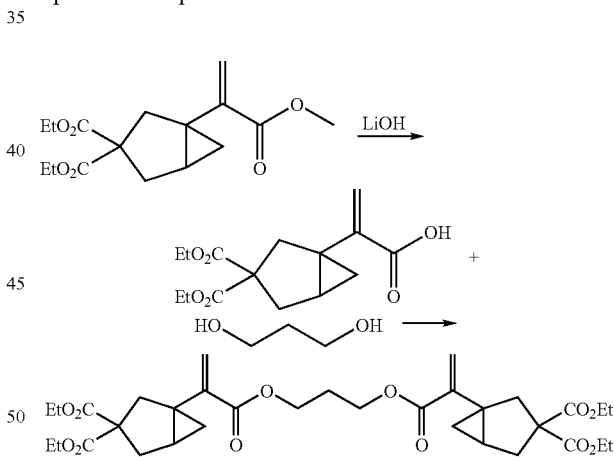

Cyclopropyl acrylates of general formula (3) (r>1, $R^{11}$=CO—O) can be obtained by hydrolysis of cyclopropyl acrylates (r=1 and $R^{10}$, X is absent, $R^{11}$=CO—O) and subsequent esterification with oligofunctional alcohols [(HO—$R^{10}$—X—)$_r$].

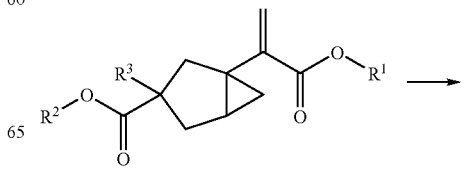

-continued
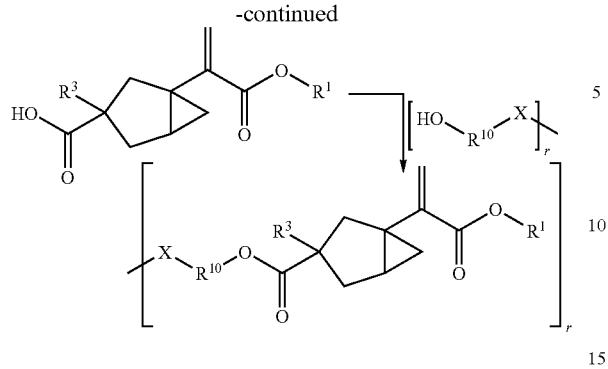
Specific Example:
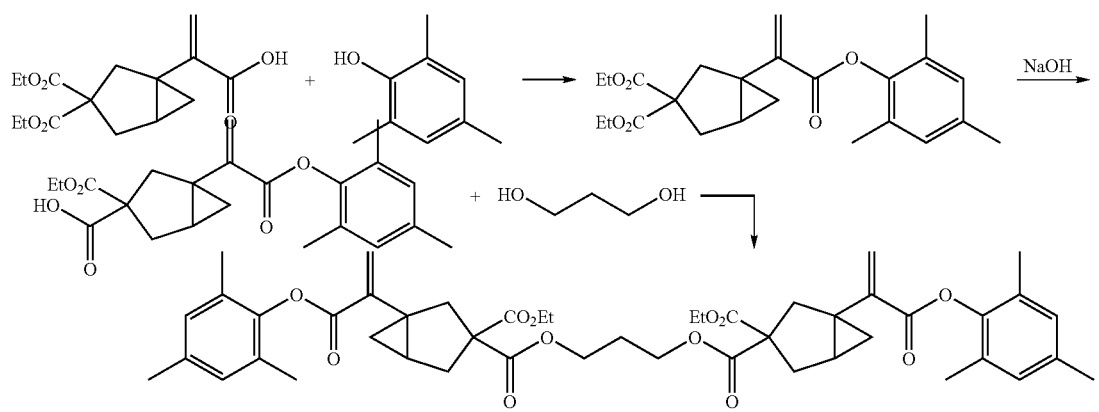
Cyclopropyl acrylates of general formula (4) (r=1, $R^{10}$, X is absent) can be obtained by cyclopropanation of 5,6-substituted bicyclo[2.2.1]hept-2-enes with diazopyruvates and subsequent WITTIG olefination (L. G. Mueller, R. G. Lawton, J. Org. Chem. 44 (1979) 4714; E. Wenkert, Helv. Chim. Acta 70 (1987) 2159:
Specific Example:
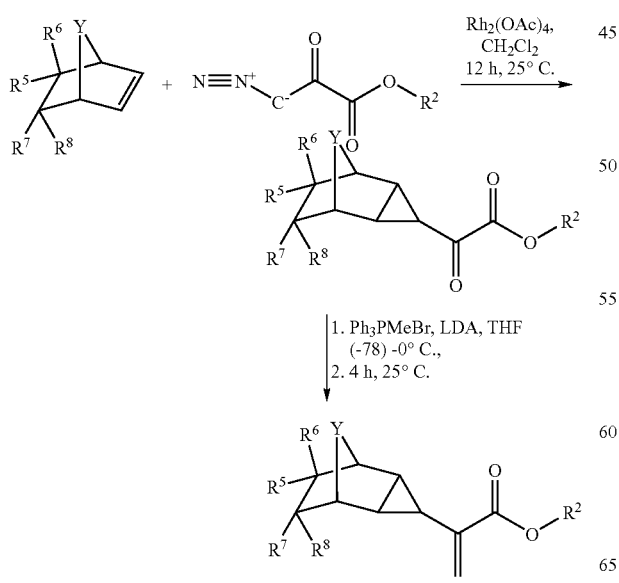
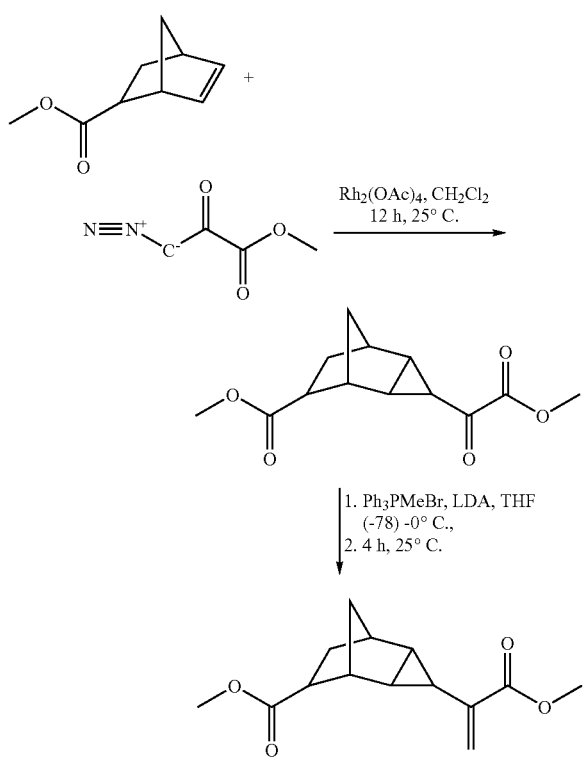

Preferred examples of the cyclopropyl acrylates according to the invention of formula (1) are:
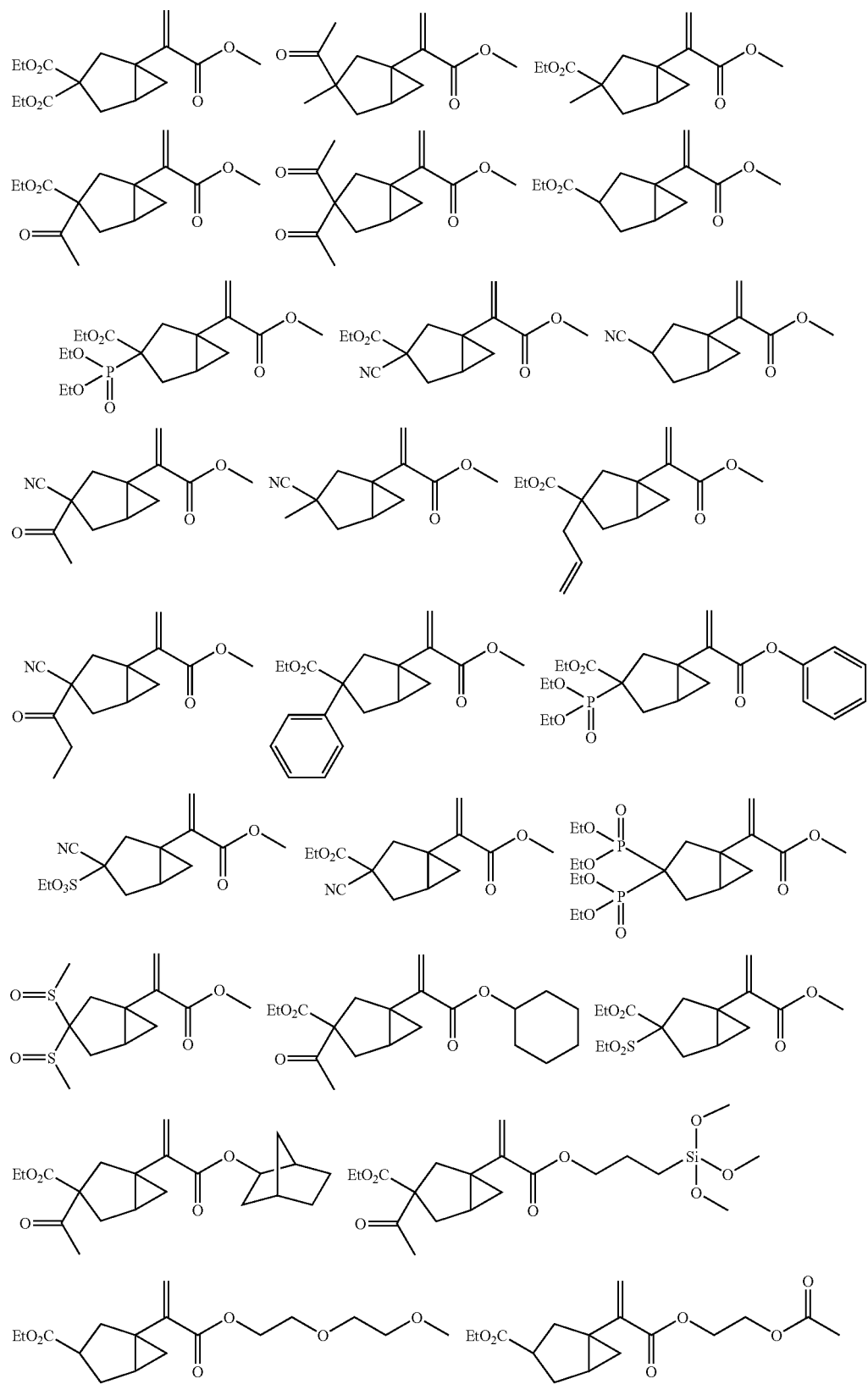

-continued
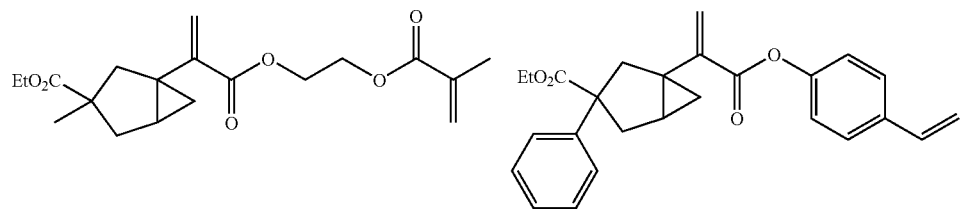
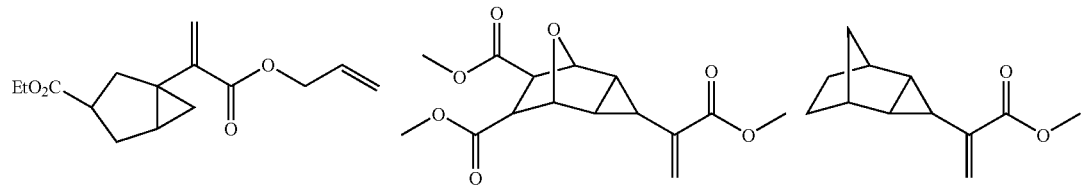
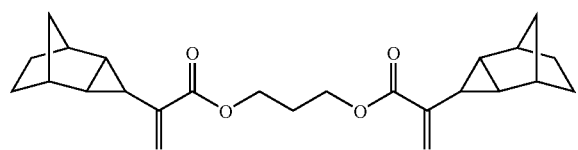
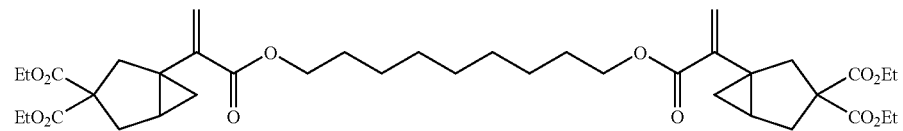
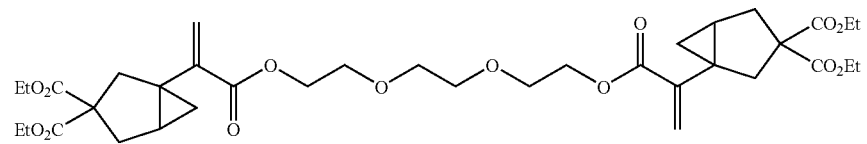
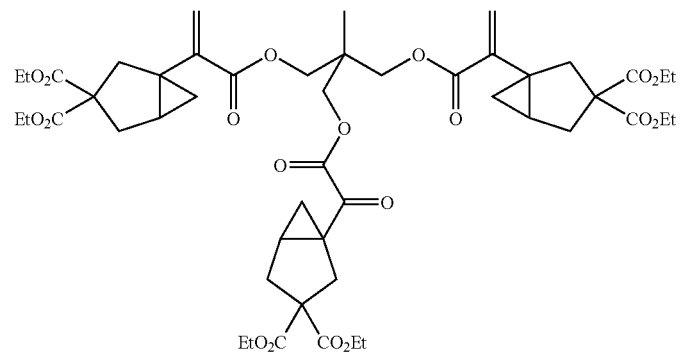
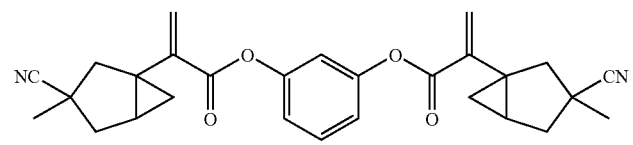

-continued

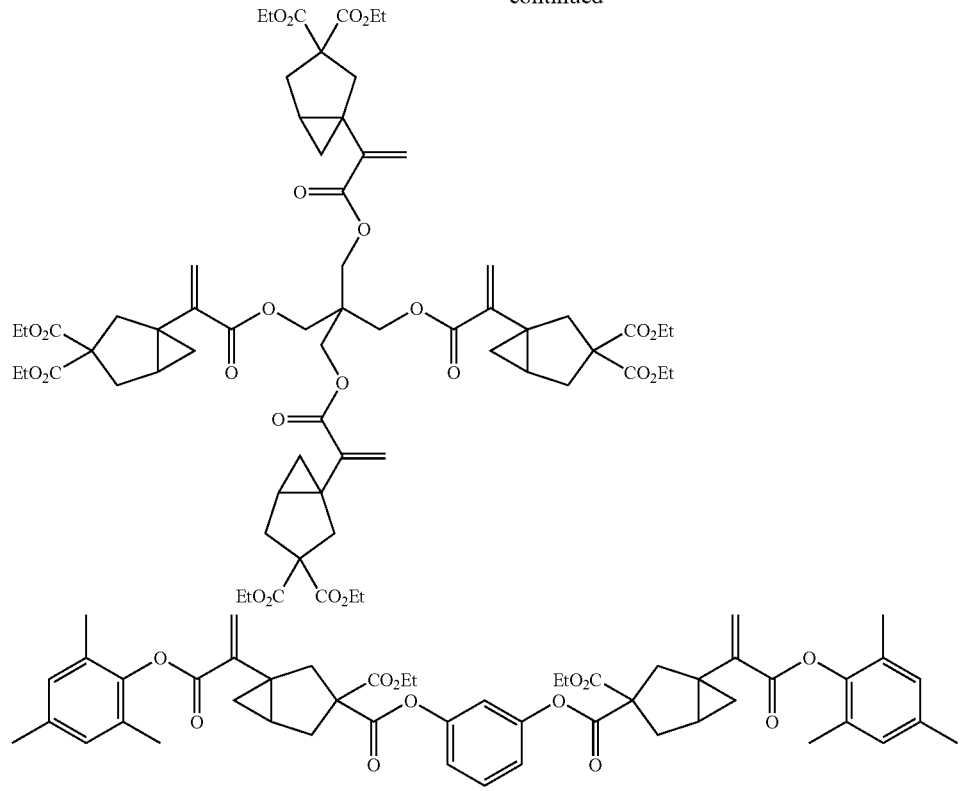

The present invention also relates to compositions which contain the cyclopropyl acrylates according to the invention.

The cyclopropyl acrylates according to the invention are particularly suitable for producing dental materials, polymers and copolymers, mouldings, adhesives, cements, filling materials, coating materials and composites in particular for dental use.

To this end they are mixed with an initiator for the radical polymerization and preferably also with additional monomers, fillers and optionally further auxiliaries. The compositions thus obtained can be cured by radical polymerization. Both the cured products, such as e.g. polymers and mouldings, and the curable compositions are also a subject of the invention.

The compositions of the invention can accordingly contain an initiator for the radical polymerization in addition to the cyclopropyl acrylate. The cyclopropyl acrylates according to the invention can be polymerized with known radical initiators (cf. Encyclopedia of Polymer Science and Engineering, Vol. 13, Wiley-Intersci. Pub., New York etc. 1988, 754ff.) accompanied by ring-opening. As initiators for the radical polymerization, azo compounds are preferably suitable, such as 2,2'-azobis(isobutyronitrile) (AIBN) or azobis-(4-cyanovaleric acid) or peroxides, such as dibenzoylperoxide, di-lauroylperoxide, tert.-butylperoctoate, tert.-butylperbenzoate or di-(tert.-butyl)-peroxide.

As initiators for the hot-curing benzpinacol and 2,2'-dialkylbenzpinacols are particularly suitable.

Moreover, photoinitiators (cf. J. P. Fouassier, J. F. Rabek (Publ.), Radiation Curing in Polymer Science and Technology, Vol. II, Elsevier Applied Science, London and New York 1993) can also be used for the UV or visible region, such as benzoin ethers, dialkylbenzilketals, dialkoxyacetophenones, acyl or bisacyl phosphinic oxides, α-diketones such as 9,10-phenanthrenequinone, diacetyl, furil, anisil, 4,4'-dichlorobenzil, 4,4'-dialkoxybenzil and camphorquinone. Camphorquinone and 2,2-dimethoxy-2-phenyl-acetophenone are preferably and α-diketones, such as camphorquinone in combination with amines as reductants, such as e.g. 4-(N,N-dimethylamino)-benzoic acid ester, N,N-dimethylaminoethylmethacrylate, N,N-dimethyl-sym.-xylidine or triethanolamine are particularly preferably used. In addition acylphosphines such as e.g. 2,4,6-trimethylbenzoyldiphenyl- or bis(2,6-dichlorobenzoyl)-4-n-propyl phenyl phosphinic oxide are also particularly suitable.

As initiators for a polymerization carried out at room temperature, redox-initiator combinations, such as e.g. combinations of benzoyl or lauroyl peroxide with N,N-di-methyl-sym.-xylidine or N,N-di-methyl-p-toluidine, are used. In addition, redox systems consisting of peroxides and reductants, such as e.g. ascorbic acid, barbiturates or sulphinic acids, are suitable.

The cyclopropyl acrylates according to the invention can be polymerized alone or in mixture with conventional radically polymerizable monomers, in particular with difunctional or multifunctional cross-linker monomers. Cross-linker monomers are compounds with two or more radically polymerizable groups. Monomers with two to three polymerizable groups are preferred.

Thus compositions according to the invention can in addition contain at least one further radically polymerizable monomer, preferably a multifunctional monomer.

For the production of adhesives, coating materials or dental materials, compositions which contain mixtures of one or more of the cyclopropyl acrylates with at least one bi- or multifunctional acrylate or methacrylate are preferably suitable, such as e.g. bisphenol-A-di(meth)acrylate, bis-GMA (an addition product of methacrylic acid and bisphenol-A-diglycidyl ether), UDMA (an addition product of 2-hydroxyethylmethacrylate and 2,2,4-trimethylhexamethylene diisocyanate), di-, tri- or tetraethylene glycol di(meth)acrylate, trimethylolpropane tri(meth)acrylate, pentaerythrite tetra(meth)acrylate, and butanedioldi(meth)acrylate, 1,10-decanedioldi(meth)acrylate and 1,12-dodecanedioldi(meth)acrylate.

Further multifunctional radically polymerizable monomers which can be contained in compositions according to the invention are e.g. urethanes made of 2-(hydroxymethyl)acrylic acid and diisocyanates, such as 2,2,4-trimethylhexamethylene diisocyanate or isophorone diisocyanate, cross-linking pyrrolidones, such as e.g. 1,6-bis(3-vinyl-2-pyrrolidonyl)-hexane, or commercially available bisacrylamides such as methylene or ethylene bisacrylamide, and/or bis(meth)acrylamide, such as e.g. N,N'-diethyl-1,3-bis(acrylamido)-propane, 1,3-bis(methacrylamido)-propane, 1,4-bis(acrylamido)-butane or N,N'-bis-(acryloyl)-piperazine, which can be synthesized by reaction from the corresponding diamines with (meth)acrylic acid chloride.

Moreover the compositions used according to the invention can contain fillers, preferably organic or inorganic particles for improving the mechanical properties or setting the viscosity. Preferred inorganic particulate fillers are amorphous spherical materials based on oxides, such as $ZrO_2$ and $TiO_2$ or mixed oxides of $SiO_2$, $ZrO_2$ and/or $TiO_2$, nanoparticulate fillers and minifillers. By nanoparticulate fillers is meant fillers with a primary particle size of approximately 5 to 100 nm, such as e.g. Aerosil 200 with a primary particle size of 12 nm. Likewise, minifillers, i.e. fillers with a particle size between 0.1 and 1.5 μm, such as e.g. finely ground quartz, glass ceramic or glass powder, and X-ray-opaque fillers, such as ytterbium trifluoride, nanoparticulate tantalum(V) oxide or barium sulphate, are preferably used as inorganic particulate fillers. In addition, glass fibres, polyamide or carbon fibres can also be used.

In addition the compositions according to the invention can if required contain further constituents, such as e.g. stabilizers, UV absorbers, colorants or pigments and lubricants.

The compositions according to the invention are particularly suitable as dental materials, in particular as dental adhesives, fixing cements or filling materials and materials for inlays/onlays, teeth or facing materials for crowns and bridges. Such materials are characterized by a smaller polymerization shrinkage and very good mechanical properties after curing.

Compositions which contain
a) 1 to 80 wt. % and particularly preferably 10 to 60 wt. % cyclopropyl acrylate according to the invention,
b) 0.01 to 5 wt. %, particularly preferably 0.1 to 2.0 wt. % initiator for the radical polymerization,
c) 0 to 60 wt. % and particularly preferably 0 to 40 wt. % further radically polymerizable monomer,
d) 0 to 40 wt. % and particularly preferably 0 to 30 wt. % solvent and
e) 0 to 20 wt. % filler are particularly suitable for use as adhesive.
Compositions which contain
a) 1 to 60 wt. % and particularly preferably 20 to 50 wt. % cyclopropyl acrylate according to the invention,
b) 0.01 to 5 wt. %, particularly preferably 0.1 to 2.0 wt. % initiator for the radical polymerization,
c) 0 to 60 wt. % and particularly preferably 0 to 20 wt. % further radically polymerizable monomer and
d) 20 to 60 wt. % and particularly preferably 30 to 60 wt. % filler are particularly suitable for use as cement.
Compositions which contain
a) 1 to 45 wt. % and particularly preferably 10 to 30 wt. % cyclopropyl acrylate according to the invention,
b) 0.01 to 5 wt. %, particularly preferably 0.1 to 2.0 wt. % initiator for the radical polymerization,
c) 0 to 50 wt. % and particularly preferably 0 to 10 wt. % further radically polymerizable monomer and
d) 30 to 85 wt. % and particularly preferably 40 to 80 wt. % filler are particularly suitable for use as filling material.
Compositions which contain
a) 1 to 95 wt. % and particularly preferably 10 to 60 wt. % cyclopropyl acrylate according to the invention,
b) 0.01 to 5 wt. %, particularly preferably 0.1 to 2.0 wt. % initiator for the radical polymerization,
c) 0 to 60 wt. % and particularly preferably 0 to 40 wt. % further radically polymerizable monomer and
d) 0 to 20 wt. % filler are particularly suitable for use as coating materials.

The invention is explained in more detail in the following with reference to embodiments.

EMBODIMENTS

Example 1

{3,3-bis(ethoxycarbonyl)bicyclo[3.1.0]hex-1-yl}methyl acrylate

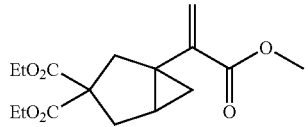

1st stage: 2-allyl-2-(4-hydroxybut-2-inyl)malonic acid diethyl ester

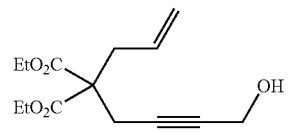

2-allyl-malonic acid ethyl ester (20 g, 100 mmol) was added in one portion to a stirred suspension of LiOH (2.51 g, 105 mmol) and LiI (2.68 g, 20 mmol) in anhydrous tetrahydrofuran (THF, 50 ml) under nitrogen and the reaction mixture was heated under reflux until it was homogeneous (approximately 30 minutes). After cooling to room temperature, 4-chloro-2-butin-1-ol (11.5 g, 110 mmol) was added and the mixture heated for another 3 hours accompanied by stirring and reflux. The mixture was again left to cool to room temperature, 25 ml of water was added, followed by extraction three times, with 50 ml ethyl acetate each time. The combined extracts were washed with 50 ml of saturated common salt solution and dried over magnesium sulphate. After evaporation of the solution under vacuum, 27 g of raw product was obtained, which was fractionally distilled at 0.001 mbar. The fraction boiling between 140 and 145° C. was pure product.

Yield: 17.5 g (63%, slightly yellowish viscous oil).

IR (film): ν=3471, 3083, 2985, 2936, 2909, 2876, 2227, 1731, 1644, 1464, 1442, 1387, 1365, 1322, 1289, 1251, 1213, 1191, 1131, 1093, 1066, 1032, 1016, 924, 858, 782, 653, 580 cm$^{-1}$.

$^1$H-NMR (250 MHz, CDCl$_3$): δ=1.24 (t, $^3$J=7.3 Hz, 6H, 2 CH$_3$), 1.90 (s, 1H, OH), 2.77 (ddd, $^3$J=7.5, $^5$J=0.9, 0.9 Hz, 2H, =CHCH$_2$), 2.81 (t, $^5$J=2.2 Hz, 2H, =CCH$_2$), 4.19 (q, $^3$J=7.3 Hz, 4H, 2 OCH$_2$), 4.21 (t, $^5$J=2.2 Hz, 2H, =CCH$_2$O), 5.11 (ddt, $^3$J=10, $^2$J=1.4, $^5$J=0.9 Hz, 1 H, =CH$_2$), 5.17 (ddt, $^3$J=17, $^2$J=1.4, $^5$J=0.9 Hz, 1H, =CH$_2$), 5.61 (ddt, $^3$J=17, 10, 7.5 Hz, 1H, —CH=) ppm.

$^{13}$C-NMR (62.9 MHz, CDCl$_3$, DEPT): δ=14.0 (2CH$_3$), 22.8 (CH$_2$), 36.4 (CH$_2$), 51.1 (CH$_2$), 56.7 (C), 61.3 (2CH$_2$), 80.5 (C), 81.5 (C), 119.8 (CH$_2$), 131.7 (CH), 169.8 (2C) ppm.

MS (70 eV, EI): m/z (%)=268 (1) [M$^+$], 251 (6) [M$^+$-OH], 239 (9) [M$^+$-C$_2$H$_5$], 227 (21) [M$^+$-C$_3$H$_5$], 223 (6) [M$^+$-C$_2$H$_5$O], 219 (6), 205 (18) [M$^+$-C$_2$H$_5$O—OH-2H], 199 (43) [M$^+$-OH—C$_4$H$_3$—H], 195 (32) [M$^+$-C$_2$H$_5$O—CO], 181 (34) [M$^+$-C$_2$H$_5$O—C$_3$H$_5$—H], 177 (92) [M$^+$-C$_2$H$_5$O—CO—OH—H], 173 (25), 165 (22), 157 (13), 153 (100) [M$^+$-C$_2$H$_5$O—CO—C$_3$H$_5$—H], 149 (74) [M$^+$-2C$_2$H$_5$—CO—H], 137 (11), 135 (38), 133 (25) [M$^+$-2C$_2$H$_5$O—CO—OH], 127 (11), 125 (41), 121 (68) [M$^+$-2C$_2$H$_5$O-2CO—H], 105 (60) [C$_8$H$_9^+$], 103 (90) [C$_8$H$_7^+$], 93 (42) [C$_7$H$_9^+$], 91 (66) [C$_7$H$_7^+$], 79 (30), 77 (42), 71 (6), 67 (7), 65 (13), 55 (11), 53 (12), 51 (5), 43 (6), 41 (18).

C$_{12}$H$_{16}$O$_3$ (208.25): calculated C, 62.67; H, 7.51. Found C, 62.42; H, 7.28.

2nd Stage: Carbonic acid-O-[5,5-bis(ethoxycarbonyl)oct-7-en-2-inyl]-O'-methyl ester

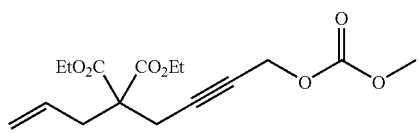

Chloroformic acid methyl ester (6.2 ml, 80 mmol, dissolved in 10 ml of dichloromethane) was added dropwise within one hour to a stirred solution of 2-allyl-2-(4-hydroxy-but-2-inyl)malonic acid diethyl ester (18.9 g, 70 mmol), NEt$_3$ (10.3 ml, 74 mmol) and DMAP (0.43 g, 3.5 mmol) in 70 ml of anhydrous dichloromethane at −10° C. under nitrogen, the temperature of the reaction mixture being kept below −5° C. Then stirring was continued for another 30 minutes at this temperature, the cooling bath was removed and most of the solvent was removed under vacuum at room temperature at most. 35 ml water and 70 ml of diethyl ether were added to the residue, the organic phase was separated off and the aqueous phase was again extracted with 2×30 ml of diethyl ether. The combined organic phases were dried over magnesium sulphate. After drawing off the solvent, 23.5 g of raw product was obtained, which was purified by flash chromatography (250 ml of flash silica gel, eluent: pentane/diethyl ether: 10:1 to 3:1. Yield: 19.8 g (87%, colourless oil).

IR (film): ν=3081, 2983, 2963, 2941, 2908, 2875, 2239, 2156, 2046, 1755, 1734, 1640, 1443, 1370, 1328, 1267, 1218, 1189, 1139, 1096, 1069, 1031, 954, 901, 861, 792 cm$^{-1}$.

$^1$H-NMR (250 MHz, CDCl$_3$): δ=1.23 (t, $^3$J=7.2 Hz, 6H, 2 CH$_3$), 2.76 (ddd, $^3$J=7.4 Hz, $^4$J=1.5 Hz, $^4$J=1 Hz, 2H, 6-H), 2.82 (t, $^5$J=2.1 Hz, 2H, 4-H), 3.79 (s, 3H, CH$_3$) 4.19 (q, $^3$J=7.2 Hz, 4H, 2CH$_2$), 4.67 (t, $^5$J=2.1 Hz, 2H, 1-H), 5.10 (ddd, $^3$J=9.9 Hz, $^2$J=1.5, $^4$J=1 Hz, 1H, 8-H$_{trans}$), 5.15 (ddd, $^3$J=17.3 Hz, $^2$J=1.5 Hz, $^4$J=1.5 Hz, 1H, 8-H$_{cis}$), 5.60 (ddd, $^3$J=17.3 Hz, $^3$J=9.9 Hz, $^3$J=7.4 Hz, 1H, 7-H).

$^{13}$C-NMR (62.9 MHz, CDCl$_3$, DEPT): δ=14.0 (2CH$_3$), 22.8 (CH$_2$), 36.4 (CH$_2$), 55.0 (CH$_3$), 55.8 (CH$_2$), 56.6 (C), 61.6 (2CH$_2$), 76.5 (C), 82.8 (C), 119.8 (CH$_2$), 131.7 (CH), 155.1 (C), 169.6 (2C).

MS (70 eV, DCI, NH$_3$): m/z (%)=670.5 (1) [2M+NH$_4^+$], 344.3 (100), [M+NH$_4^+$], 327.3 (9) [M+H$^+$], 251.2 (4), 177 (2).

C$_{16}$H$_{22}$O$_7$ (326.34): calculated C, 58.89; H, 6.79. Found C, 58.58; H, 7.08.

3rd Stage: {3,3-bis(ethoxycarbonyl)bicyclo[3.1.0]hex-1-yl}methyl acrylate

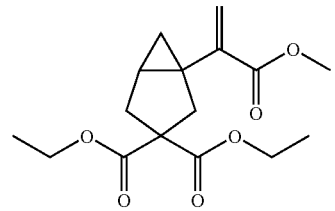

PD(OAc)$_2$ (224 mg, 1.0 mmol) was added to a solution of tris(2-furyl)phosphane (505 mg, 2.2 mmol) and tetramethylammonium bromide (167 mg, 1.1 mmol) in degassed methanol (300 ml) and the mixture was stirred at room temperature for 1 hour. Then carbonic acid-O-[5,5-bis(ethoxycarbonyl) oct-7-en-2-inyl]-O'-methyl ester (7.35 g, 22.5 ml) was added and carbon monoxide introduced. The mixture was stirred under 1 bar carbon monoxide pressure at room temperature for 2 days and then the solvent was removed under vacuum. The raw product was chromatographically purified on 100 ml of flash silica gel with pentane/ether (10:1 to 5:1).

Yield: 6.03 g (86%), colourless oil.

IR (film): ν=3074, 2983, 2957, 2908, 2878, 1728, 1629, 1438, 1384, 1367, 1325, 1295, 1245, 1212, 1198, 1177, 1124, 1092, 1069, 1058, 1018, 1000, 955, 898, 861, 817, 766, 696 cm$^{-1}$.

$^1$H-NMR (250 MHz, CDCl$_3$): δ=0.52 (dd, $^2$J=5.6 Hz, $^3$J=4.5 Hz, 1H, 6-H$_{endo}$), 0.74 (ddd, $^3$J=7.9 Hz, $^2$J=Hz $^4$J=1.5 Hz, 1H, 6-H$_{exo}$), 1.51-1.59 (m, 1H, 1-H), 1.21 (t, $^3$J=7.2 Hz, 3H, CH$_3$), 1.24 (t, $^3$J=7.2 Hz, 3H, CH$_3$), 2.51-2.62 (m, 3H), 2.71 (d, $^2$J=13.5 Hz, 1H), 3.75 (s, 3H, OCH$_3$), 4.15 (q, $^3$J=7.2 Hz, 2H, OCH$_2$), 4.17 (q, $^3$J=7.2 Hz, 2H, =OCH$_2$), 5.59 (d, $^2$J=1.2 Hz, 1H, 3'-H$_{trans}$), 6.15 (d, $^2$J=1.2 Hz, 1H, 3'-H$_{cis}$).

$^{13}$C-NMR (62.9 MHz, CDCl$_3$, DEPT): δ=13.9 (2CH$_3$), 16.3 (CH$_2$), 24.9 (CH), 31.2 (C), 6.0 (CH$_2$), 40.2 (CH$_2$), 51.8 (CH$_3$), 59.9 (C), 61.6 (CH$_2$), 61.7 (CH$_2$), 125.8 (CH$_2$), 142.2 (C), 167.0 (C), 171.6 (C), 172.9 (C).

MS (70 eV, EI): m/z (%)=310 (8) [M$^+$], 279 (17), 278 (55), 265 (36), 250 (25), 236 (20), 218 (4), 205 (15), 190 (55), 177 (100), 163 (32), 149 (18), 147 (26), 131 (43), 105 (26), 103 (81), 91 (12), 79 (12), 77 (20), 65 (3), 59 (4), 55 (4), 53 (3), 51 (2), 41 (3).

$C_{16}H_{22}O_6$ (310.34): calculated C, 61.92; H, 7.15. Found C, 61.57; H, 7.36.

Example 2

2-(3-acetyl-3-ethoxycarbonyl-bicyclo[3.1.0]hex-1-yl)methyl acrylate (ABHCE)

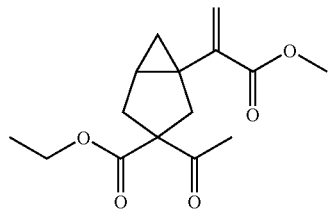

1st stage: 2-acetyl-2-allyl-6-hydroxy-hex-4-yne acid ethyl ester

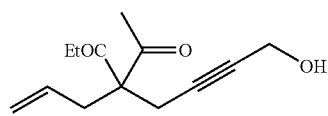

2-Allyl-ethyl acetoacetate (34.2 g, 200 mmol) was added in one portion to a stirred suspension of LiOH (5.03 g, 210 mmol) and LiI (5.35 g, 40 mmol) in anhydrous THF (100 ml) under nitrogen and the reaction mixture was heated under reflux until it was homogeneous (approximately 30 minutes). After cooling to room temperature, 4-chloro-2-butin-1-ol (23 g, 220 mmol) was added and the mixture heated for another 3 hours accompanied by stirring and reflux. The mixture was again left to cool to room temperature, 50 ml of water was added, followed by extraction three times, with 100 ml of ethyl acetate each time. The combined extracts were washed with 100 ml of saturated common salt solution and dried over magnesium sulphate. After evaporation of the solution under vacuum, 47.6 g of raw product was obtained, which was fractionally distilled at 0.002 mbar. The fraction boiling between 120 and 130° C. was pure product. Yield: 38.3 g (78%, slightly yellowish viscous oil).

IR (film): ν=3440, 3078, 2985, 2935, 2875, 2227, 1739, 1717, 1640, 1437, 1414, 1393, 1355, 1321, 1278, 1212, 1179, 1130, 1092, 1053, 1015, 927, 856, 779 cm$^{-1}$.

$^1$H-NMR (250 MHz, CDCl$_3$): δ=1.25 (t, $^3$J=7.1 Hz, 3H, CH$_3$), 1.96 (s, 1H, OH), 2.16 (s, 3H, CH$_3$), 2.70 (dddd, $^2$J=14.3, $^3$J=7.5, $^4$J=1.2, 0.9 Hz, 1H, CHCH$_2$, AB system), 2.77 (t, $^5$J=2.1 Hz, 2H, ≡CCH$_2$), 2.79 (dddd, $^2$J=14.3, $^3$J=7.5, $^4$J=1.2, 0.9 Hz, 1H, ≡CHCH$_2$, AB system), 4.20 (t, ($^5$J=2.1 Hz, 2H, ≡CCH$_2$O), 4.21 (q, $^3$J=7.1 Hz, 2H, OCH$_2$), 5.11 (ddt, $^3$J=9.8, $^2$J=1.9, $^4$J=0.9 Hz, 1H, =CH$_2$), 5.16 (ddt, $^3$J=17, $^2$J=1.9, $^4$J=1.2 Hz, 1H, =CH$_2$), 5.55 (ddt, $^3$J=17, 9.8, 7.5 Hz, 1H, —CH=) ppm.

$^{13}$C-NMR (62.9 MHz, CDCl$_3$, DEPT): δ=14.0 (CH$_3$), 21.9 (CH$_2$), 26.5 (CH$_3$), 35.7 (CH$_2$), 51.0 (CH$_2$), 61.8 (CH$_2$), 62.6 (C), 80.5 (C), 81.8 (C), 199.8 (CH$_2$), 131.5 (CH$_2$), 170.4 (C), 202.8 (C) ppm.

MS (70 eV, DCI, NH$_3$): m/z (%)=494 (3) [2M+NH$_4^+$], 256 (100) [M+NH$_4^+$], 239 (2) [M+H$^+$].

$C_{13}H_{18}O_4$ (238.28): calculated C, 65.53; H, 7.61. Found C, 65.40; H, 7.46.

2nd Stage: Carbonic acid-O-[5-acetyl-5-ethoxycarbonyl-oct-7-en-2-inyl]-O'-methyl ester

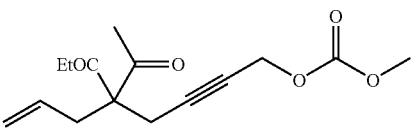

Chloroformic acid methyl ester (17 ml, 170 mmol, dissolved in 10 ml of dichloromethane) was added dropwise within one hour to a stirred solution of 2-acetyl-2-allyl-6-hydroxy-hex-4-yne acid ethyl ester (38.1 g, 160 mmol), NEt$_3$ (23.3 ml, 167 mmol) and DMAP (0.98 g, 3 mmol) in 160 ml of anhydrous dichloromethane at −10° C. under nitrogen, the temperature of the reaction mixture being kept below −5° C. The mixture was then stirred for another 30 minutes at this temperature, the cooling bath was removed and most of the solvent was removed under vacuum at room temperature at most. 80 ml water and 200 ml of diethyl ether were added to the residue, the organic phase was separated off and the aqueous phase was extracted another two times with 50 ml of diethyl ether in each case. The combined organic phases were dried over magnesium sulphate. After drawing off the solvent, 47 g of raw product was obtained, which was purified by flash chromatography (450 ml of flash silica gel, eluent:pentane/diethyl ether: 10:1 to 3:1. Yield: 45 g (95%, colourless oil).

IR (film): ν=3083, 2990, 2963, 2858, 2238, 2161, 2052, 1755, 1717, 1640, 1443, 1371, 1267, 1207, 1179, 1135, 1092, 1070, 1015, 1054, 954, 899, 856, 790 cm$^{-1}$.

$^1$H-NMR (250 MHz, CDCl$_3$): δ=1.25 (t, $^3$J=7.1 Hz, 3H, CH$_3$), 2.15 (s, 3H, CH$_3$), 2.69 (dtdd, $^2$J=15.0, $^3$J=7.4, $^4$J=1.2, 1.0 Hz, 6-H, AB system), 2.77 (t, $^5$J=2.2 Hz, 2H, 4-H), 2.79 (dtdd, $^2$J=15.0, $^3$J=7.4, $^4$J=1.2, 1.0 Hz, 1H, 6-H, AB system), 3.79 (s, 3H, CH$_3$), 4.20 (q, $^3$J=7.1 Hz, 2H, CH$_2$), 4.66 (t, $^5$J=2.2 Hz, 2H, 1-H), 5.10 (ddt, $^3$J=9.7, $^2$J=1.8, $^4$J=1.0 Hz, 1H, 8-H$_{trans}$), 5.15 (ddt, $^3$J=17.0, $^2$J=1.8, $^4$J=1.2 Hz, 1H, 8-H$_{cis}$), 5.51 (ddd, $^3$J=17.0, $^3$J=9.7 Hz, $^3$J=7.4 Hz, 1H, 7-H) ppm.

$^{13}$C-NMR (62.9 MHz, CDCl$_3$, DEPT): δ=14.0 (CH$_3$), 21.9 (CH$_2$), 26.5 (CH$_3$), 35.8 (CH$_2$), 55.0 (CH$_3$), 55.7 (CH$_2$), 61.8 (CH$_2$), 62.5 (C), 76.7 (C), 82.8 (C), 119.9 (CH$_2$), 131.4 (CH), 155.1 (C), 170 (C), 202.5 (C) ppm.

MS (70 eV, EI): m/z (%)=296 (1) [M$^+$], 259 (2), 257 (8) 254 (40) [M$^+$-C$_2$H$_2$O—], 250 (6), 223 (7), 221 (41) [M$^+$-CH$_3$O—CO$_2$], 202 (14), 191 (9), 178 (100) [M$^+$-CH$_3$OH—C$_2$H$_2$O—CO$_2$], 175 (24), 169 (6), 163 (6), 149 (36), 147 (63) [M$^+$-C$_2$H$_5$O—CO$_2$—CH$_3$OH—CO], 137 (13), 135 (8), 133 (16), 131 (14), 127 (4), 123 (9), 121 (7), 119 (6), 109 (7), 107 (8), 105 (46), [C$_8$H$_9^+$], 103 (18) [C$_8$H$_7^+$], 91 (13) [C$_7$H$_7^+$], 79 (11) [C$_6$H$_7^+$], 77 (14) [C$_6$H$_5^+$], 65 (2), 59 (4), 43 (42), [C$_2$H$_3$O$^+$], 41 (2).

$C_{15}H_{20}O_6$ (296.32): calculated C, 60.80; H, 6.80. Found C, 61.16; H, 6.77.

3rd Stage: 2-(3-acetyl-3-ethoxycarbonyl-bicyclo [3.1.0]hex-1-yl}methyl acrylate

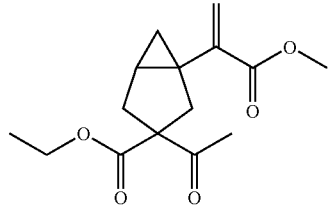

PD(OAc)$_2$ (694.4 mg, 3.1 mmol) was added to a solution of tris(2-furyl)phosphane (1.581 g, 6.8 mmol) and tetramethylammonium bromide (527 mg, 3.4 mmol) in 800 ml of degassed methanol and the mixture was stirred at room temperature for 1 hour. Then carbonic acid-O-(5-acetyl-5-ethoxycarbonyl-oct-7-en-2-inyl)-O'-methyl ester (45 g, 152 mmol) was added and carbon monoxide introduced. The mixture was vigorously stirred under a carbon monoxide atmosphere at 25° C., until the starting material was completely reacted (63 hours, GC monitoring). The methanol was distilled off under vacuum and 45 g of raw product was obtained, which was further purified by flash chromatography (450 ml of flash silica gel, pentane/diethyl ether, 8:1 to 4:1). Yield: 1st fraction: 4 g (purity approximately 90%) and 35.3 g (83%, GC: 98%, slightly yellowish oil. Finally ball-tube distillation was carried out (140° C.; 0.001 mbar).

Yield: 30.6 g (72%; GC: 98.5%, colourless oil).

IR (film): ν=3078, 2985, 2952, 2875, 1717, 1624, 1437, 1355, 1289, 1234, 1212, 1163, 1124, 1092, 1070, 1015, 993, 954, 856, 812, 773, 691 cm$^{-1}$.

Main isomer: $^1$H-NMR (250 MHz, CDCl$_3$): δ=0.35 (dd, $^2$J=5.6, $^3$J=4.5 Hz, 1H, 6-H$_{endo}$), 0.67 (dddd, $^3$J=7.8, $^2$J=5.6, $^4$J=1.5, $^4$J=1.5 Hz, 1H, 6-H$_{exo}$), 1.22 (t, $^3$J=7.1 Hz, 3H, CH$_3$), 1.48-1.55 (m, 1H, 5-H), 2.15 (s, 3H, CH$_3$), 2.40-2.70 [m, 4H, 2(4)-H], 3.75 (s, 3H, CH$_3$), 4.15 (q, $^3$J=7.1 Hz, 2H, CH$_2$), 5.59 (d, $^2$J=1.4 Hz, 1H, =CH$_2$), 6.15 (d, $^2$J=1.4 Hz, 1H, =CH$_2$) ppm.

$^{13}$C-NMR (62.9 MHz, CDCl$_3$, DEPT): δ=14.0 (CH$_3$), 16.4 (CH$_2$), 24.8 (CH), 26.6 (CH), 31.2 (C), 34.5 (CH$_2$), 38.8 (CH$_2$), 51.8 (CH$_3$), 61.8 (CH$_2$), 67.0 (C), 125.8 (CH$_2$), 142.1 (C), 167.0 (C), 171.9 (C), 204.6 (C) ppm.

Secondary isomer: $^1$H-NMR (250 MHz, CDCl$_3$): δ=0.49 (dd, $^2$J=5.6, $^3$J=4.5 Hz, 1H, 6-H$_{endo}$), 0.76 (dddd, $^3$J=7.8, $^2$J=5.6, $^4$J=1.5, $^4$J=1.5 Hz, 1H, 6-H$_{exo}$), 1.26 (t, $^3$J=7.1 Hz, 3H, CH$_3$), 1.47-1.54 (m, 1H, 5-H), 2.13 (s, 3H, CH$_3$), 2.40-2.70 [m, 4H, 2(4)-H], 3.74 (s, 3H, CH$_3$), 4.19 (q, $^3$J=7.1 Hz, 2H, CH$_2$), 5.61 (d, $^2$J=1.4 Hz, 1H, =CH$_2$), 6.16 (d, $^2$J=1.4 Hz, 1H, =CH$_2$) ppm.

$^{13}$C-NMR (62.9 MHz, CDCl$_3$, DEPT): δ=14.0 (CH$_3$), 16.4 (CH$_2$), 24.9 (CH), 25.9 (CH), 31.1 (C), 34.5 (CH$_2$), 38.6 (CH$_2$), 51.8 (CH$_3$), 61.8 (CH$_2$), 67.1 (C), 126.1 (CH$_2$), 142.0 (C), 166.9 (C), 173.4 (C), 202.1 (C) ppm.

MS (70 eV, EI): m/z (%)=280 (12) [M$^+$], 248 (100) [M$^+$CH$_3$O—H], 237 (20) [M$^+$-CH$_3$CO], 234 (56) [M$^+$-C$_2$H$_5$O—H], 220 (37) [M$^+$-CH$_3$O—CO—H], 206 (19) [M$^+$-C$_2$H$_5$O—CO—H], 191 (61) [M$^+$-CH$_3$O—C$_2$H$_5$—CO—H], 177 (70) [M$^+$-CH$_3$CO—CH$_3$O—CO—H], 175 (28), 163 (18) [M$^+$-C$_2$H$_5$O—CH$_3$CO—CO—H], 159 (16), 154 (16), 149 (34), 146 (78) [M$^+$-C$_2$H$_5$O—CH$_3$CO-2CO-2H], 131 (55) [M$^+$-C$_2$H$_5$O—CH$_3$CO—CH$_3$O—CO-2H], 119 (8), 105 (61) [C$_8$H$_9^+$], 103 (84) [C$_8$H$_7^+$], 91 (19) [C$_7$H$_7^+$], 79 (18), 77 (24) [C$_6$H$_5^+$], 59 (5), 55 (5), 43 (94) [C$_2$H$_3$O$^+$].

C$_{15}$H$_{20}$O$_5$ (280.32): calculated Cm 64.27; H, 7.19. Found 63.92; H, 7.12.

Example 3

Radical Solvent Polymerization of the Functionalized Cyclopropyl Acrylate ABHCE from Example 2

2.0 mol. % (relative to the monomer) of azobisisobutyronitrile (AIBN) was added to a solution of the cyclopropyl acrylate from Example 2 (ABHCE) (2.0 mol/l) in chlorobenzene in a Schlenk vessel. After degassing of the monomer solution and closure of the Schlenk vessel under argon, polymerization was carried out in a thermostatically controlled water bath at 65° C. After 1 or 15 hours the polymerization was discontinued by precipitation of the polymerisate with ten times the quantity of hexane. The polymer formed was filtered off and dried until its weight was constant. The yield was almost 58 or 95% of a white homopolymer with a numerically average molar mass of 296.000 or 434.400 g/mol and a glass-transition temperature of 90° C. or 97° C.

The $^1$H and $^{13}$C-NMR spectra of the polymers formed prove that the polymerization of ABHCE proceeded accompanied by opening of the cyclopropane ring.

Example 4

Radical Copolymerization of the Functionalized Cyclopropyl Acrylate from Example 2 (ABHCE) with Methylmethacrylate (MMA)

Analogously to the homopolymerization in solution (Example 3) a monomer mixture of the cyclopropyl acrylate from Example 2 (ABHCE) (1.0 mol/l), methylmethacrylate (MMA, 1.0 mol/l) and AIBN (2.5 mol. %) was prepared in chlorobenzene and polymerized. The yield of copolymer was 5.4% after 15 minutes. A molar copolymer composition of ABHCE:MMA=1.00:1.13 was ascertained by $^1$H-NMR spectroscopy. This result demonstrates a reactivity of the cyclopropyl acrylate ABHCE comparable with the methacrylate MMA.

Example 5

Radical Copolymerization of the Functionalized Cyclopropyl Acrylate from Example 2 (ABHCE) with UDMA In order to measure the polymerization shrinkage a mixture of 50 wt. % of the cyclopropyl acrylate from Example 2 (ABHCE) and 50 wt. % of UDMA (urethane dimethacrylate from 2 mol 2-hydroxyethylmethacrylate and 1 mol 2,2,4-trimethyl hexamethylene diisocyanate) was prepared, 0.3 wt. % (relative to the total mixture) of camphorquinone (photoinitiator) and 0.5 wt. % 4-(dimethylamino)-ethyl benzoate (amino accelerator) were added and the mixture then irradiated with a dental light source (Spectramat, Ivoclar Vivadent AG). From the difference in the measured densities of the monomer mixture or the polymerisate formed, taking into account the polymerization shrinkage of pure UDMA ($\Delta V_P$=6.1%), a polymerization shrinkage of only 5.1% was calculated. The polymerization shrinkage of 20.7% known for MMA was calculated from the results of the polymerization of an analogous mixture of MMA and UDMA (50:50).

Examples 4 and 5 show that the functionalized cyclopropyl acrylates according to the invention are characterized by a reactivity similar to that of methacrylates, but unlike methacrylates produce a very small polymerization shrinkage.

Example 6

Preparation of a Dental Cement Based on the Cyclopropyl Acrylate from Example 2 (ABHCE)

Corresponding to Table 1 below, a composite fixing cement based on (A) a methacrylate mixture (comparison) and (B) the monomer ABHCE from Example 2 was prepared by means of an "Exakt" roll mill (Exakt Apparatebau, Norderstedt). Corresponding testpieces of the materials measuring 2×2×25 mm were prepared, which were cured by being irradiated twice for 3 minutes each time, by a dental light source (Spectramat, Ivoclar Vivadent AG). The mechanical properties of the cured testpieces were then ascertained according to ISO Standard 4049.

Table 2 shows that the cured material B according to the invention corresponds to the comparison material A in every respect in its mechanical properties.

The example shows that dental materials based on functional cyclopropyl acrylates such as ABHCE according to the invention, in spite of a similar reactivity and greatly reduced polymerization shrinkage, display no disadvantages in respect of the mechanical properties.

TABLE 1

Composition of the cements

| Substance | Material A[1] Contents (wt. %) | Material B Contents (wt. %) |
|---|---|---|
| UDMA | 31.6 | 31.6 |
| 1,10-decanediol-dimethacrylate | 7.8 | — |
| Monomer from Example 2 (ABHCE) | — | 7.8 |
| Aerosil OX-50 (Degussa) | 41.3 | 41.3 |
| Ytterbium trifluoride (Rhone-Poulenc) | 18.7 | 18.7 |
| Photoinitiator[2] | 0.5 | 0.5 |

[1]Comparative example
[2]1:1 mixture of camphorquinone and p-N,N-dimethylaminoethyl benzoate

TABLE 2

Mechanical properties of the cements

| Mechanical property | Material A[1] | Material B |
|---|---|---|
| Bending strength (MPa) after 24 hours | 95 | 99 |
| Bending strength (MPa) after 24 hours WS[2] | 101 | 99 |
| Bending strength (MPa) after 7 days WS | 111 | 108 |
| Bending E modulus (GPa) after 24 hours | 4.76 | 4.78 |
| Bending E modulus (GPa) after 24 hours WS | 4.93 | 4.56 |
| Bending E modulus (GPa) after 7 days WS | 5.13 | 4.70 |

[1]Comparative example
[2]WS = testpieces stored in water at 37° C.

Example 7

Preparation of a Filling Composite Based on the Cyclopropyl Acrylate from Example 2 (ABHCE)

Corresponding to Table 3 below, a filling composite D based on a methacrylate mixture and the monomer ABHCE from Example 2 was prepared by means of an LPM 0.1 laboratory kneader (Linden, Marienheide). Testpieces of the materials measuring 2×2×25 mm were prepared, which were cured by being irradiated twice for 3 minutes each time, by a dental light source (Spectramat, Ivoclar Vivadent AG). The mechanical properties of the cured testpieces were then ascertained according to ISO Standard 4049.

The dilatometrically ascertained polymerization shrinkage was only 2.2% whilst, for a comparative composite C, in which the monomer ABHCE according to the invention was replaced by the usual dimethacrylate diluent 1,10-decanediol-dimethacrylate ($D_3MA$), a polymerization shrinkage of 3.2% was measured.

The example shows that filling materials based on the cyclopropyl acrylates like ABHCE according to the invention have good mechanical properties.

TABLE 3

Composition of the filling materials

| | Contents (wt. %) | |
|---|---|---|
| Substance | Composite C[1] | Composite D |
| SR-348C (Sartomer)[2] | 7.2 | 7.2 |
| 1,10-decanediol-dimethacrylate | 10.3 | — |
| ABHCE | — | 10.3 |
| Glass filler GM27884[3] | 51.2 | 51.2 |
| Aerosil OX-50 (Degussa) | 1.0 | 1.0 |
| Ytterbium trifluoride (Rhone-Poulenc) | 14.9 | 14.9 |
| Spherosil[4] | 14.2 | 14.2 |
| Photoinitiator[5] | 0.2 | 0.2 |

[1]Comparative example
[2]Ethoxylated bisphenol-A-dimethacrylate with a total of 3 ethylene oxide units
[3]Barium-aluminium silicate glass (Schott) silanized, average particle size 1.2 μm
[4]$SiO_2$—$ZrO_2$ mixed oxide with a primary particle size of approximately 200 nm (Tokoyama Soda)
[5]Mixture of camphorquinone (0.05%), p-N,N-dimethylaminoethyl benzoate (0.08%) and Lucirin TPO (0.07%, BASF).

TABLE 4

Mechanical properties of the filling materials

| Mechanical property | Composite C[1] | Composite D |
|---|---|---|
| Bending strength (MPa) after 24 hours | 144 | 112 |
| Bending strength (MPa) after 24 hours WS[2] | 145 | 120 |
| Bending strength (MPa) after 7 days WS | 140 | 112 |
| Bending E modulus (GPa) after 24 hours | 9.55 | 9.65 |
| Bending E modulus (GPa) after 24 hours WS | 9.24 | 9.30 |
| Bending E modulus (GPa) after 7 days WS | 9.18 | 9.70 |

[1]Comparative example
[2]WS = testpieces stored in water at 37° C.

The invention claimed is:

1. Cyclopropyl acrylates of general formula (1'), (1") and (1'''), constitutional and stereoisomers thereof and their mixtures

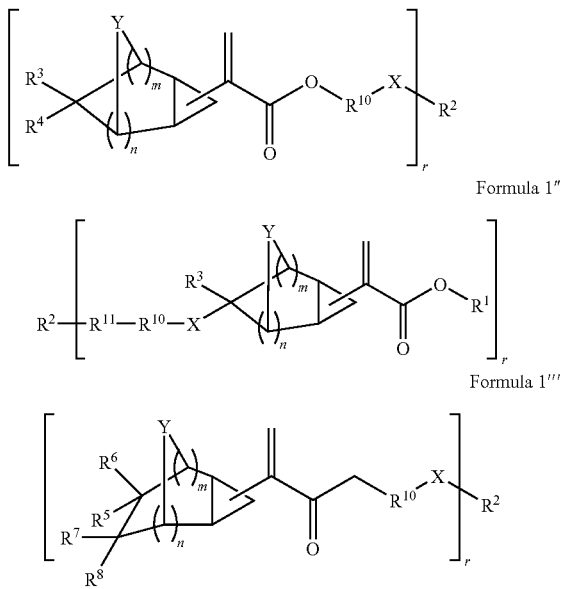

Formula 1'

Formula 1"

Formula 1''' wherein the variables have the following meanings independently of each other:

Y=for Formula (1') or (1"): is absent, $CH_2$ or O,
for Formula (1'''): $CH_2$ or O,
n=for Y is absent: 0, 1, 2 or 3,
for Y=$CH_2$ or O:1,
m=for Y is absent: 0, 1, 2 or 3,
for Y=$CH_2$ or O:1,
r=1, 2, 3 or 4,
$R^1$=H, a $C_1$ to $C_{10}$ alkyl, $C_6$ to $C_{12}$ aryl, $C_1$ to $C_{10}$ arylalkyl or bicyclic $C_5$-$C_{12}$ radical,
$R^2$=for r=1: an aliphatic $C_1$-$C_{20}$ hydrocarbon radical, substituted r times by the expression in brackets, which can be interrupted by O or S, cycloaliphatic $C_4$-$C_{12}$ radical, bicyclic $C_5$-$C_{12}$ radical, $C_6$-$C_{14}$ aryl or $C_7$-$C_{20}$ alkylaryl radical,
for r=2, 3, 4: an aliphatic $C_1$-$C_{20}$ hydrocarbon radical, substituted r times by the expression in brackets, which can be interrupted by O or S, cycloaliphatic $C_4$-$C_{12}$ radical or a bicyclic $C_5$-$C_{12}$ radical,
$R^3$=—CO—$OR^9$, —CO—$R^9$, —S(O)$R^9$, $SO_2R^9$, —$SO_2$($OR^9$), —PO($OR^9$)$_2$, —CN, —H, or —$R^9$,
$R^4$=-CO—$OR^9$, —CO—$R^9$, —S(O)$R^9$, $SO_2R^9$, —$SO_2$($OR^9$), —PO($OR^9$)$_2$, or —CN,
$R^5$—$R^8$=independently of one another H, —CO—$OR^9$, —CO—$NHR^9$, —CO—$NR^9_2$, —CO—$R^9$, —CN, a $C_1$-$C_{20}$ alkyl radical which can be interrupted by O or S, a cycloaliphatic $C_4$-$C_{12}$ radical, a bicyclic $C_5$-$C_{12}$ radical, a $C_6$-$C_{14}$ aryl, $C_7$-$C_{20}$ alkylaryl radical, or at least two of the radicals form together with the carbon atoms to which they are bonded a 5- to 8-membered ring system,
$R^9$=a $C_1$-$C_{20}$ alkyl radical which can be interrupted by O or S, a cycloaliphatic $C_4$-$C_{12}$ radical, a bicyclic $C_5$-$C_{12}$ radical, a $C_6$-$C_{14}$ aryl or $C_7$-$C_{20}$ alkylaryl radical,
$R^{10}$=is absent or a $C_1$-$C_{20}$ alkylene radical which can be interrupted by O or S, a cycloaliphatic or bicyclic $C_5$-$C_{12}$ radical, a $C_6$-$C_{14}$ arylene or $C_7$-$C_{20}$ alkylenearylene radical,
$R^{11}$=—COO—, —CO—, —SO—, —$SO_2$—, —$SO_2$(O—), —PO($OR^9$) or (O—),
X=is absent, —O—CO—, —CO—O—, —NH—CO—, —CO—NH—, —NH—CO—O— or —O—CO—NH—, wherein X has the meaning "is absent" if $R^{10}$ is absent, $R^{10}$ cannot be absent if X is present, and
wherein the radicals $R^2$ and $R^{5-9}$ can be substituted or unsubstituted,
and
wherein several radicals of one type can be identical or different.

2. Cyclopropyl acrylate according to claim 1, wherein the substituents of the radicals $R^2$ and $R^{5-9}$ are selected from alkyl, halogen, $OCH_3$, $OC_2H_5$, vinyl, (meth)acryl, $COOR^{12}$, $SiCl_3$, $Si(OR^{13})_3$, and mesogenic groups, wherein
$R^{12}$=H or $C_1$ to $C_{10}$ alkyl, $C_6$ to $C_{12}$ aryl, $C_6$ to $C_{10}$ arylalkyl or a bicyclic $C_5$-$C_{12}$ radical and
$R^{13}$=H or $C_1$ to $C_{10}$ alkyl radical.

3. Cyclopropyl acrylate according to claim 1, in which the cyclopropyl acrylate has Formula (1') and Y is absent.

4. Cyclopropyl acrylate according to claim 1, in which the cyclopropyl acrylate has Formula (1") and Y is absent.

5. Cyclopropyl acrylate according to claim 1, in which the cyclopropyl acrylate has Formula (1''').

6. Cyclopropyl acrylate according to claim 1, in which at least one variable of formula (1'), (1") or (1''') has one of the following meanings:
Y=Formula (1') or (1"): is absent,
Formula (1'''): $CH_2$ or O,
n=1,
m=1,
r=1 or 2,
$R^1$=H, $C_1$ to $C_5$ alkyl or bicyclic $C_5$-$C_{12}$ radical,
$R^2$=an aliphatic $C_1$-$C_6$ hydrocarbon radical which can be interrupted by O, a cycloaliphatic $C_6$-$C_8$ radical, a bicyclic $C_6$-$C_8$ radical, a $C_6$-$C_{10}$ aryl or $C_7$-$C_{10}$ alkylaryl radical,
$R^3$=—CO—$OR^9$, —CO—$R^9$, $SO_2R^9$, CN, H or —$R^9$,
$R^4$=—CO—$OR^9$, —CO—$R^9$, $SO_2R^9$, or CN,
$R^5$—$R^8$=independently of one another H, —CO—$OR^9$, —CO—$R^9$, CN, a $C_1$-$C_6$ alkyl radical which can be interrupted by O, a cycloaliphatic $C_6$-$C_8$ radical, a bicyclic $C_6$-$C_8$ radical, a $C_6$-$C_{10}$ aryl or $C_7$-$C_{10}$ alkylaryl radical,
$R^9$=a $C_1$-$C_6$ alkyl radical which can be interrupted by 0, a cycloaliphatic $C_6$-$C_8$ radical, a bicyclic $C_6$-$C_8$ radical, a $C_6$-$C_{10}$ aryl or $C_7$-$C_{10}$ alkylaryl radical,
$R^{10}$=is absent or a $C_1$-$C_{10}$ alkylene radical which can be interrupted by O, a bicyclic $C_6$-$C_9$ radical, or $C_7$-$C_{10}$ alkylenearylene radical,
$R^{11}$=—CO—O—, —CO— or —$SO_2$—,
X=is absent, —O—OC— or —CO—O—.

7. Composition which contains a cyclopropyl acrylate according to claim 1.

8. Composition according to claim 7 which additionally contains an initiator for the radical polymerization.

9. Composition according to claim 7 which additionally contains at least one further radically polymerizable monomer.

10. Composition according to claim 9 which additionally contains a multifunctional monomer as radically polymerizable monomer.

11. Composition according to claim 10 which, as multifunctional radically polymerizable monomer, contains a bi- or multifunctional acrylate or methacrylate, bisphenol-A-di(meth)acrylate, bis-GMA (an addition product of methacrylic acid and bisphenol-A-diglycidyl ether), UDMA (an addition product of 2-hydroxyethylmethacrylate and 2,2,4-trimethylhexamethylene diisocyanate), di-, tri- or tetraethylene glycol di(meth)acrylate, trimethylolpropane tri(meth)acrylate, pentaerythrite tetra(meth)acrylate, butanedioldi(meth)acrylate, 1,10-decanedioldi(meth)acrylate or 1,12-dodecanedioldi(meth)acrylate, a urethane of 2-(hydroxymethyl)acrylic acid and diisocyanates, such as 2,2,4-trimethylhexamethylene diisocyanate or isophorone diisocyanate, a cross-linking pyrrolidone, such as 1,6-bis(3-vinyl-2-pyrrolidonyl)-hexane, a bisacrylamide, methylene or ethylene bisacrylamide, bis(meth)acrylamide, N,N'-diethyl-1,3-bis(acrylamido)-propane, 1,3-bis(methacrylamido)-propane, 1,4-bis(acrylamido)-butane, N,N'-bis-(acryloyl)-piperazine, or a mixture of two or more of these monomers.

12. Composition according to claim 7 which additionally contains filler.

13. Composition which contains
a) 1 to 80 wt. % cyclopropyl acrylate according to claims 1,
b) 0.01 to 5 wt. % initiator for the radical polymerization,
c) 0 to 60 wt. % radically polymerizable monomer,
d) 0 to 40 wt. % solvent and
e) 0 to 20 wt. % filler.

14. Composition which contains
a) 1 to 60 wt. % cyclopropyl acrylate according to claims 1,
b) 0.01 to 5 wt. % initiator for the radical polymerization,
c) 0 to 60 wt. % radically polymerizable monomer and
d) 20 to 60 wt. % filler.

15. Composition which contains
a) 1 to 45 wt. % cyclopropyl acrylate according to claims 1,
b) 0.01 to 5 wt. % initiator for the radical polymerization,
c) 0 to 50 wt. % radically polymerizable monomer and
d) 30 to 85 wt. % filler.

16. Composition which contains
a) 1 to 95 wt. % cyclopropyl acrylate according to claims 1,
b) 0.01 to 5 wt. % initiator for the radical polymerization,
c) 0 to 60 wt. % radically polymerizable monomer and
d) 0 to 20 wt. % filler.

17. Composition according to claim 7 which additionally contains at least one further constituent selected from the group consisting of stabilizers, UV absorbers, colorants, pigments and lubricants.

18. A method for using a cyclopropyl acrylate according to claim 1 for preparing a dental material.

19. A method for using a composition according to claim 7 as dental material.

20. The method according to claim 18, wherein the dental material is an adhesive.

21. The method according to claim 18, wherein the dental material is a cement.

22. The method according to claim 18, wherein the dental material is a filling material.

23. The method according to claim 18, wherein the dental material is a coating material.

24. Cyclopropyl acrylate according to claim 6, wherein $R^9$=$C_1$-$C_3$ alkyl.

25. Cyclopropyl acrylate according to claim 6, wherein $R^{10}$=$C_1$-$C_6$ alkylene.

26. Cyclopropyl acrylate according to claim 6, wherein $R^{11}$=—CO—O—.

* * * * *